US008207137B2

(12) United States Patent
Trochon et al.

(10) Patent No.: US 8,207,137 B2
(45) Date of Patent: Jun. 26, 2012

(54) METHOD OF INHIBITING ANGIOGENESIS OR INVASION OR FORMATION OF METASTASES

(75) Inventors: Véronique Trochon, Paris (FR); He Lu, Epinary-sur-Seine (FR); Claudine Soria, Taverny (FR)

(73) Assignee: INSERM (FR)

(*) Notice: Subject to any disclaimer, the term of this patent is extended or adjusted under 35 U.S.C. 154(b) by 83 days.

(21) Appl. No.: 10/764,628

(22) Filed: Jan. 26, 2004

(65) Prior Publication Data
US 2004/0171549 A1 Sep. 2, 2004

Related U.S. Application Data

(63) Continuation of application No. PCT/FR02/02691, filed on Jul. 26, 2002.

(30) Foreign Application Priority Data

Jul. 26, 2001 (FR) ...................... 01 10015

(51) Int. Cl.
A61K 48/00 (2006.01)
C12N 15/00 (2006.01)
C12N 15/12 (2006.01)

(52) U.S. Cl. .................. 514/44 R; 435/320.1; 536/23.1; 536/23.5

(58) Field of Classification Search ........................ None
See application file for complete search history.

(56) References Cited

U.S. PATENT DOCUMENTS

| 5,814,609 | A  | * | 9/1998  | Markland et al. ............... 514/12 |
| 6,294,368 | B1 | * | 9/2001  | Merkulov et al. .............. 435/219 |
| 7,074,408 | B2 | * | 7/2006  | Fanslow et al. ............. 424/185.1 |
| 2002/0077465 | A1 | * | 6/2002 | Shi et al. ....................... 536/23.2 |
| 2002/0165377 | A1 | * | 11/2002 | Ruben et al. .................. 435/226 |
| 2003/0194797 | A1 | * | 10/2003 | Young et al. .................. 435/226 |
| 2006/0177443 | A1 | * | 8/2006 | Fanslow et al. ............. 424/144.1 |

FOREIGN PATENT DOCUMENTS

| EP | 1 803 810 A1 | 7/2007 |
| JP | 2003-523768 A | 8/2003 |
| WO | 01/62905 A2 | 8/2001 |

OTHER PUBLICATIONS

Verma, I.M. and Somia, N. Gene Therapy—promises, problems and prospects, Sep. 1997, Nature, vol. 369, pp. 239-242.*
Protein structure prediction—Wikipedia, downloaded Oct. 14, 2005.*
Tertiary structures—Biology Pages, downloaded Oct. 14, 2005.*
Smith et al, Surface point mutations that significantly alter the structure and stability of a protein's denatured state, Protein Science, 1996, vol. 5, pp. 2009-2019.*
Gura, T, Systems for identifying New Drugs Are Often Faulty, Science, 1997, vol. 2788, pp. 1041-1042.*
Verma and Somia, Gene Therapy—promises,problems and prospects, Nature, 1997, vol. 389, pp. 239-242.*
Russell, Replicating Vectors for Gene Therapy of Cancer: Risks, Limitations and Prospects, European j Cancer, 1994. vol. 30A(8), pp. 1165-1171.*
Mir,. Nucleic Acids Electrotransfer-Based Gene Therapy (Electrogenetherapy): Past, Current, and Future, Molecular Biotechnology Part B of Applied Biochemistry and Biotechnology, 2009, vol. 43(2), pp. 167-176.*
Greciet et al, BioAlliance Pharma announces positive preliminary phase I clinical results with its AMEP biotherapy for metastatic melanoma, posted Sep. 2011, downloaded Sep. 26, 2011.*
Bettan et al, Efficient DNa electrotrasnfer into tumors, Bioelectrochemistry, 2000, vol. 52, pp. 83-90.*
Meng and El-Deiry, Tumor Suppressor Genes as Targets for Cancer Gene Therapy, Gene Therapy of Cancer, Chapter 1, pp. 3-18, 1999.*
Gura et al, Systems for Identifying New Drugs are Often Faulty, Sicence, 1997, vol. 278, pp. 1041-1042.*
Jörn Krätzschmar et al., *Metargidin, a Membrane-anchored Metalloprotease-Disintegrin Protein with an RGD Integrin Binding Sequence*, The Journal of Biological Chemistry, vol. 271, No. 9, Mar. 1, 1996, pp. 4593-4596 (XP000644305).
Barbara Herren et al., *Expression of a disintegrin-like protein in cultured human vascular cells and in vivo*, The FASEB Journal for Experimental Biology, vol. 11, Feb. 1997, pp. 173-180 (XP002201316).
Xi-Ping Zhang et al., *Specific Interaction of the Recombinant Disintegrin-like Domain of MDC-15 (Metargidin, ADAM-15) with Integrin αvβ3*, The Journal of Biological Chemistry, vol. 273, No. 13, Mar. 27, 1998, pp. 7345-7350 (XP002201315).
Chia Hsin Yeh et al. *Accutin, a New Disintegrin, Inhibits Angiogenesis In Vitro and In Vivo by Acting as Integrin $\alpha_{IIb}\beta_1$ Antagonist and Indusing Apoptosis*, Blood, vol. 92, No. 9, Nov. 1, 1998, pp. 3268-3276 (XP002201317).
Brooks, P.C. et al., "Requirement of Vascular Integrin $\alpha_v\beta_3$ for Angiogenesis," *Science*, Apr. 1994, vol. 264, pp. 569-571.
Cai, S. et al., "ADAM 23/MDC3, a Human Disintegrin that Promotes Cell Adhesion via Interaction with the $\alpha_1\beta_3$ Integrin through an RGD-Independent Mechanism," *Molecular Biology of the Cell*, Apr. 2000, vol. 11, pp. 1457-1469. Nath, D. et al., "Interaction of Metargidin (ADAM-15) with $\alpha_v\beta^3$ and $\alpha_5\beta_1$ Integrins on Different Haemopoietic Cells," *Journal of Cell Science*, 1999, vol. 112, pp. 579-587.
Eliceiri, B.P. et al., "Integrin αvβ3 Requirement for Sustained Mitogen-Activated Protein Kinase Activity during Angiogenesis," *The Journal of Cell Biology*, Mar. 1998, vol. 140, No. 5, pp. 1255-1263.
Eliceiri, P.B. et al., "Role of αv Integrins during Angiogenesis, " *The Cancer Journal*, 2000, vol. 6, (suppl. 3), pp. S245-S249.
Eto, K. et al., "RGD-Independent Binding of Integrin α9β1 to the ADAM-12 and -15 Disintegrin Domains Mediates Cell-Cell Interaction," *The Journal of Biological Chemistry*, Nov. 2000, vol. 275, No. 45, pp. 34922-34930.
Folkman, J., "What Is the Role of Endothelial Cells in Angiogenesis?" *Laboratory Investigation*, 1984, vol. 51, No. 6, pp. 601-604.
Frisch S.M., "Anoikis," *Methods in Enzymology*, 2000, vol. 322, pp. 472-479.

(Continued)

Primary Examiner — Maria Marvich
(74) Attorney, Agent, or Firm — DLA Piper LLP (US)

(57) ABSTRACT

A method of inhibiting angiogenesis or invasion or formation of metastases in a mammal including administering a therapeutically effective amount of an active agent selected from the group consisting of a protein substance including all or part of a disintegrin domain of an adamalysin or a derivative thereof, a nucleic acid molecule including a polynucleotide sequence coding all or part of the disintegrin domain of an adamalysin or a derivative thereof to the mammal.

5 Claims, 10 Drawing Sheets

OTHER PUBLICATIONS

Hammes, H-P. et al., "Subcutaneous Injection of a Cyclic Peptide Antagonist of Vitronectin Receptor-Type Integrins Inhibits Retinal Neovascularization," *Nature Medicine*, May 1996; vol. 2, No. 5, pp. 529-533.

Howard, I. et al., "Interaction of the Metalloprotease Disintegrins MDC9 and MDC15 with Two SH3 Domain-Containing Proteins, Endophilin 1 and SH3PX1," *The Journal of Biological Chemistry*, Oct. 1999, vol. 274, No. 44, pp. 31693-31699.

Jaffe, E.A. et al., "Synthesis of Antihemophilic Factor Antigen by Cultured Human Endothelial Cells, " *The Journal of Clinical Investigation*, Nov. 1973, vol. 52, pp. 2757-2764.

Kang, I-C. et al., "A Novel Disintegrin Salmosin Inhibits Tumor Angiogenesis," *Cancer Research*, Aug. 1999, vol. 59, pp. 3754-3760.

Klein, S. et al., "Basic Fibroblast Growth Factor Modulates Integrin Expression in Microvascular Endothelial Cells," *Molecular Biology of the Cell*, Oct. 1993, vol. 4, pp. 973-982.

Kostetsky, P.V. et al., "Conformational Analysis of the Biologically Active RGD-Containing Anti-Adhesive Peptide Cyclo (ArgGlyAsp-Phe-*D*-Val)," *Biochemistry*, 2000, vol. 65, No. 9, pp. 1041-1048.

Mir, L.M. et al., "High-Efficiency Gene Transfer into Skeletal Muscle Mediated by Electric Pulses," *Proc. Natl. Acad. Sci. USA*, Apr. 1999, vol. 96, pp. 4262-4267.

Nehls, V. et al., "The Configuration of Fibrin Clots Determines Capillary Morphogenesis and Endothelial Cell Migration," *Microvascular Research*, 1996, vol. 51, article No. 0032, pp. 347-364.

O'Reilly, M.S. et al., "Angiostatin: A Novel Angiogenesis Inhibitor that Mediates the Suppression of Metastases by Lewis Lung Carcinoma," *Cell*, Oct. 1994, vol. 79, pp. 315-328.

O'Reilly, M.S. et al., "Endostatin: An Endogenous Inhibitor of Angiogenesis and Tumor Growth," *Cell*, Jan. 1997, vol. 88, pp. 277-285.

Pepper, M.S. et al., "Chondrocytes Inhibit Endothelial Sprout Formation In Vitro: Evidence for Involvement of a Transforming Growth Factor-Beta," *Journal of Cellular Physiology*, 1991, vol. 146, pp. 170-179.

Primakoff, P. et al., "The ADAM Gene Family Surface Proteins with Adhesion and Protease Activity," *TIG*, Feb. 2000, vol. 16, No. 2, pp. 83-87.

Sim, B.K.L. et al., "A Recombinant Human Angiostatin Protein Inhibits Experimental Primary and Metastatic Cancer," *Cancer Research*, Apr. 1997, vol. 57, pp. 1329-1334.

Sim, B.K.L. et al., "Angiostatin and Endostatin: Endogenous Inhibitors of Tumor Growth," *Cancer Metastasis Reviews*, 2000, vol. 19, pp. 181-190.

Smith, D.B. et al., "Single-Step Purification of Polypeptides Expressed in *Escherichia coli* as Fusions with Glutathion S-Transferase," *Gene* , 1988, vol. 67, pp. 31-40.

Trochon-Joseph, V. et al., "Evidence of Antiangiogenic and Antimetastatic Activities of the Recombinant Disintegrin Domain of Metargidin," *Cancer Research*, Mar. 2004, pp. 2062-2069.

Wolfsberg, T.G. et al., "ADAM, a Novel Family of Membrane Proteins Containing ADisintegrin And Metalloprotease Domain: Multipotential Functions in Cell-Cell and Cell-Matrix Interactions," *The Journal of Cell Biology*, 1995, vol. 131, pp. 275-278.

Wu, Z. et al., "Suppression of Tumor Growth with Recombinant Murine Angiostatin," *Biochemical and Biophysical Research Communications*, 1997; vol. 236, article No. RC977032, pp. 651-654.

Yamaguchi, N. et al., "Endostatin Inhibits VEGF-induced Endothelial Cell Migration and Tumor Growth Independently of Zinc Binding," *The EMBO Journal*, 1999, vol. 18, No. 16, pp. 4414-4423.

Zhou, M. et al., "MDC-9 (ADAM-9/Meltrin γ) Functions as an Adhesion Molecule by Binding the $\alpha_v\beta_5$ Integrin," *Biochemical and Biophysical Research Communications*, 2001, vol. 280, pp. 574-580.

Zhu, Z. et al., "Anoikis and Metastatic Potential of Cloudman S91 Melanoma Cells," *Cancer Research*, Feb. 2001, vol. 61, pp. 1707-1716.

Trikha, M. et al., "Contortrostatin, a Snake Venom Disintegrin, inhibits β1 Integrin-Mediated Human Metastatic Melanoma Cell Adhesion and Bocks Experimental Metastasis," *Cancer Research*, 1994, vol. 54, pp. 4993-4998.

Kuno, K. et al., "Molecular Cloning of a Gene Encoding a New Type of Metalloproteinase-Disintegrin Family Protein with Thrombospondin Motifs as an Inflammation Associated Gene," *The Journal of Biological Chemistry*, issue of Jan. 3, 1997, vol. 272, No. 1, pp. 556-562.

Vazquez, F. et al., "METH-1, a Human Ortholog of ADAMTS-1, and METH-2 Are Members of a New Family of Proteins with Angio-Inhibitory Activity," *The Journal of Biological Chemistry*, issue of Aug. 13, 1999, vol. 274, No. 33, pp. 23349-23557.

Rochlitz, Christoph F., "Gene Therapy of Cancer," *Swiss Med. Wkly*, 2001, vol. 131, pp. 4-9.

* cited by examiner

METHOD OF INHIBITING ANGIOGENESIS OR INVASION OR FORMATION OF METASTASES

RELATED APPLICATION

This is a continuation of International Application No. PCT/FR02/02691, with an international filing date of Jul. 26, 2002 (WO 03/009866, published Feb. 6, 2003, which is based on French Patent Application No. 01/10015, filed Jul. 26, 2001.

TECHNICAL FIELD

Our technology relates to a method of inhibiting angiogenesis or invasion or formation of metastases implicated in numerous pathologies such as cancer, inflammatory diseases, atherosclerosis and pathological angiogenesis of the retina.

SUMMARY

We provide a method of inhibiting angiogenesis or invasion or formation of metastases in a mammal including administering a therapeutically effective amount of an active agent selected from the group consisting of a protein substance including all or part of a disintegrin domain of an adamalysin or a derivative thereof, a nucleic acid molecule including a polynucleotide sequence coding all or part of the disintegrin domain of an adamalysin or a derivative thereof to the mammal.

We also provide methods of treating cancer, inflammatory diseases, atherosclerosis, macular degeneration and psoriasis in mammals including administering a therapeutically effective amount of an active agent selected from the group consisting of a protein substance including all or part of a disintegrin domain of an adamalysin or a derivative thereof and a nucleic acid molecule including a polynucleotide sequence coding all or part of the disintegrin domain of an adamalysin or a derivative thereof to the mammal.

BRIEF DESCRIPTION OF THE DRAWINGS

Other advantages and characteristics of our technology will become clear from the description below pertaining to the preparation AMEP and its in vitro and in vivo antiangiogenic, anti-invasive and antimetastatic activity, and in which reference will be made to the attached drawings in which:

in FIG 1a, the visualization of the fusion protein (glutathione-S transferase-AMEP) in SDS-PAGE after purification. A single band is visible after staining with Coomassie blue at 36 kDa. In FIG. 1b, a Western blot of purified AMEP. Visualization of a single band at 10 kDa by an anti-disintegrin antiserum performed in the rabbit.

DETAILED DESCRIPTION

Figure 1:
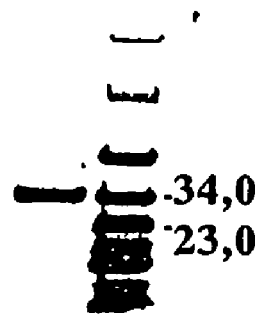
FIG. 1 represents.
Figure 1:

We demonstrate the anti-angiogenic, anti-invasive and anti-metastatic functions of a fragment of a molecule present on human endothelial cells. We also disclose the use of an adamalysin fragment constituted by all or part of the disintegrin domain, more particularly, the use of the disintegrin domain of metargidin (Krätzschmar et al., 1996) also referred to below as "AMEP" which stands for "antiangiogenic metargidin peptide".

Compared to other antiangiogenic substances that have been described in the literature, this fragment:
  simultaneously inhibits all of the stages of angiogenesis:
    migration and proliferation of endothelial cells, their adhesion to different matrix substrates and formation of capillary structures, and
  induces an apoptosis of the endothelial cells.

Furthermore, in an unexpected manner, this fragment has the capacity, on the one hand, to inhibit the invasion of cancerous cells and, on the other hand, to prevent formation of metastases, notably of cells that express the integrin alpha v beta 3 at their surface.

Angiogenesis designates a morphogenetic process by which new blood capillaries are formed by budding of existing vessels in response to a stimulation. During angiogenesis in vivo, the neocapillaries are born from capillaries or post-capillary venules, but not from arteries, arterioles or veins. Thus, an angiogenic factor is a molecule that enables initiation and/or maintenance of angiogenesis, such as, for example FGF2. An antiangiogenic factor is, thus, a molecule that inhibits angiogenesis by acting on one or more key stages of angiogenesis.

Adhesions consist of the capacity of cells to attach themselves to an extracellular matrix. This phenomenon involves numerous adhesion molecules present at the surface of the cells.

The migration of cells causes the intervention of enzymes which enable the cells to degrade the compounds of the matrix as well as the adhesion molecules which provide for anchoring the cells to the matrix. Moreover, the dynamic architecture of the cytoskeleton enables the cells to alternate the periods of adhesion and detachment indispensable for motility.

Proliferation is a phenomenon which relates to the division of cells over time.

Apoptosis consists of the intrinsic capacity of normal cells to trigger their own suicide according to a complex program referred to as cell death. Anoikis is a form of induced apoptosis in normal cells resulting from a loss of their adhesion to the substrate.

Invasion is an excessive multiplication of a class of anatomic elements which leads to the replacement by these elements of adjacent elements.

Metastasis is a focus of cancerous cells related to a preexisting cancer, referred to as primary, but developed remotely from this primary focus without continuity with it. The dissemination of these secondary foci takes place via lymphatic or hematic routes.

The development of a tumor and its dissemination in various organs depends on intra- and perivascular vascularization, also called angiogenesis (Folkman, 1984). Targeting the angiogenic process is a new therapeutic approach and represents a revolution in the treatment of cancer. Numerous antiangiogenic molecules are presently involved in clinical trials.

Vitaxin is humanized anti-integrin alpha v beta 3 antibody which induces an inhibition of the proliferation of endothelial cells as well as a proapoptotic effect (Brooks et al., 1994; Hammes et al., 1996). However, it does not modify their migration. Integrin alpha v beta 3 is an adhesion molecule expressed preferentially by the endothelial cells of neovessels and certain cancerous cells. It interacts with certain compounds of the extracellular matrix notably vitronectin, fibronectin, laminin collagen IV and the fibrin inducing the adhesion and migration of endothelial cells. The major role of integrin alpha v beta 3 in angiogenesis has been described in detail (review, Eliceiri and Cheresh, 2000).

Marimastat blocks the proteolytic activity of the metalloproteinases and thereby inhibits the migration of endothelial cells, but has no effect on their proliferation. The metalloproteinases (MMPs) belong to the large family of enzymes that enable degradation of the group of compounds of the extracellular matrix indispensable for migration of endothelial cells. Other enzymes, belonging to the serine proteases, also participate in cell migration such as urokinase plasminogen activator (uPA) when it is bound to its receptor anchored to the membrane surface (u-PAR) and plasmin.

This group of drugs has the goal of blocking angiogenesis, but their action is limited to one or two stages of this process in contrast to AMEP which is multipotent. Thus, AMEP blocks not only the set of angiogenic functions of the integrin alpha v beta 3, against which it is directed initially, i.e., proliferation and adhesion of endothelial cells, but, surprisingly, it also induces a complete inhibition of migration of these cells as well as an inhibition of formation of capillary structures. Its originality is, thus, based on its proapoptotic effect on these cells independent of a modification of their cell cycle.

Moreover, in an unexpected manner, AMEP possesses both noteworthy anti-invasive and antimetastatic capacities.

The adamalysins, also referred to as ADAM for "a disintegrin and metalloprotein" or MDC for "metalloprotein-rich, disintegrin-rich and cysteine-rich protein" are a family of proteins anchored in the plasma membrane of cells. The structure common to the group of 29 adamalysins comprises:
- a metalloproteinases domain the protease catalytic activity of which is zinc dependent,
- a disintegrin domain, and
- a domain rich in cysteine and in EGF type repetition (Wolfsberg et al., 1995).

It should be noted, however, that out of the group of adamalysins, only about ten have a metalloproteinase domain possessing a catalytic activity. The physiological role of the different adamalysins is extremely varied: regulation of cell adherence, release of a ligand, activation of a receptor, cell fusion (review, Primakoff and Myles, 2000). However, the mode of action of these molecules remains unknown.

AMEP should be differentiated from the snake disintegrins which have been described in the literature from two points of view:
- the snake disintegrins exert a limited action on the different stages of angiogenesis. For example, accutin (Yeh et al., 1998) inhibits the adhesion of endothelial cells to different components of the matrix and induces their apoptosis whereas salmosin (Kang et al., 1999) induces an inhibition of the adhesion of endothelial cells and of their proliferation induced by FGF2.

AMEP also has the advantage of being of human origin and, consequently, not having the antigenic character of the snake disintegrins which exhibit an immunogenic character that prevents them from being used as drugs in long-term therapy required in anticancer treatment.

Thus, we provide a drug for inhibiting angiogenesis or invasion and/or formation of metastases of an active agent selected from among a protein substance comprising or constituted by all or part of the disintegrin domain of an adamalysin or a derivative thereof, a nucleic acid molecule comprising or constituted by a polynucleotide sequence coding all or part of the disintegrin domain of an adamalysin or a derivative thereof.

The adamalysin is advantageously metargidin. Consequently, the invention pertains most particularly to a protein substance comprising or constituted in part or entirely by the disintegrin domain of metargidin the amino acid sequence of which is represented in SEQ ID NO. 2 or a derivative thereof.

The AMEP fragment is remarkable in that it is capable of inhibiting tumoral invasion, formation of metastases and all of the stages of angiogenesis, i.e., both the migration and proliferation of endothelial cells—in contrast to the assumptions of certain authors (Zhang et al., 1998) whose opinion was that the disintegrin domain by binding the integrin alpha v beta 3 could be implicated solely in the homotypic aggregation of endothelial cells during angiogenesis. Moreover, the inhibitory action of AMEP on angiogenesis is observed in the absence of any addition of angiogenic factors.

The necessity of using exogenous angiogenic factors is seen, in contrast, when demonstrating the antiangiogenic effect of anti-alpha v beta 3 antibodies. They inhibit angiogenesis solely after induction by FGF2, an angiogenic factor indispensable for maintaining angiogenesis (Klein et al., 1993). The therapeutic value of AMEP—compared to other peptides possessing the RGD sequence described as simple inhibitors of the adhesion of endothelial cells (Kostesky and Artemjev, 2000)—is also based on its spectrum of action.

We provide the disintegrin domain of an adamalysin, more particularly, metargidin and derivatives thereof. Such derivatives constitute functional equivalents having antiangiogenic, anti-invasive and/or antimetastatic properties that one skilled in the art can determine from this disclosure and, more particularly, from the models and tests presented in the experimental part below. The derivatives can be fragments of truncated form, sequences modified by deletion, addition, suppression or replacement of one or more amino acids. The derivatives can also be fragments corresponding to said derivatives constituted by chemically modified amino acids, these modifications making the derivatives more stable. The invention also pertains to polynucleotide sequences coding for said derivatives.

Our technology, thus, also pertains most especially to a nucleic acid molecule comprising a polynucleotide sequence coding all or part of the disintegrin domain of metargidin the sequence in SEQ ID NO. 1 or a derivative thereof. The coding sequence of this domain is constituted by 276 nucleotides (Met-420 to Glu-511).

The sequence is advantageously placed under the control of regulation sequences of its expression. Such a nucleic acid molecule is, for example, a vector such as:

- an expression plasmid coding for the antiangiogenic fragment AMEP or a derivative irrespective of the transfer technique,
- an expression plasmid coding for a protein of fusion between the fragment or a derivative and protein domain facilitating purification (pGEX type plasmid) or facilitating tissue targeting,
- a plasmid or other type of expression vector coding for the AMEP fragment or a derivative, specific of a host organism other than a bacterium, for example, a baculovirus, in an insect cell or a plasmid in a eukaryote cell.

Such a nucleic acid molecule can be used in gene therapy or cell therapy protocols comprising administering the molecule or cells transformed by the molecule to an individual in a manner to express all or part of the disintegrin domain at the level of a site to be treated.

Such a nucleic acid molecule is also useful for preparing the protein substance of the invention. Thus, human AMEP was synthesized from bacteria and eukaryote cells transformed with a plasmid coding for AMEP. More precisely, *Escherichia coli* (clone DH5 alpha) was used as bacterial production system and the muscle tibia cranial as eukaryote production system, but yeast or any other production system could be used.

The demonstration of the inhibitory action of AMEP on all of the stages of angiogenesis (migration, proliferation, adhesion, apoptosis of the endothelial cells and the formation of capillary type structures) and on the tumoral invasion and the formation metastases makes it possible to offer a new antitumor drug in the treatment of cancers. In fact, in contrast to the other inhibitors of angiogenesis described in the literature to date, AMEP exerts an intrinsic anti-invasive, antimetastatic and antiangiogenic activity which is multipotent and exceptional. It inhibits both migration and proliferation of endothelial cells of different origins (macrovascular or microvascular, transformed or not transformed) as well as adhesion of cells (on fibrinogen, vitronectin and fibronectin) and formation of capillary type structures in three-dimensional models in vitro. A proapoptotic affect of AMEP has also been demonstrated. In vivo, AMEP blocks tumor growth by inhibiting formation of blood vessels and metastatic dissemination, in particular, of cells expressing the integrin alpha v beta 3.

We, thus, offer a new method for treating and/or preventing cancer pathologies in general as well as diseases in which angiogenesis contributes to the pathogenesis of the diseases such as inflammatory diseases, psoriasis, atherosclerosis, macular degeneration and the like.

The active agent is combined in the drugs with any pharmaceutically acceptable vehicle known in the art and suitable for the mode of administration employed. Thus, the drugs can be administered:

- alone, via the systemic, local or oral route or as an implant;
- by cell or gene therapy;
- in combination with other active principles;
- in any pharmaceutical form whatsoever, such as, for example, a nanoparticle form.

The description below uses conventional molecular biology techniques described in the literature, such as, for example: Sambrook, Fritsch and Maniatis, *Molecular Cloning; A Laboratory Manual*, Second Edition (1989), Cold Spring Harbor Laboratory Press, Cold Spring Harbor, N.Y. (Sambrook et al., 1989); *DNA Cloning: A Practical Approach*, Volumes I and II (D. N. Glover ed., 1985; B. Perdal, *A Practical Guide to Molecular Cloning* (1984); F. M. Ausubel et al. (editors) *Current Protocols in Molecular Biology*, John Wiley and Sons, Inc. (1994), all the disclosures of which are all incorporated by reference.

Thus, the term "nucleic acid" is understood to mean a chimeric compound comprising subunits linked covalently and called nucleotides. The nucleic acids include ribonucleic acid (RNA) and deoxyribonucleic acid (DNA), both of which can appear as a single or double strand. The DNAs include cDNA (complementary), genomic DNA, synthetic DNA and semisynthetic DNA. The sequence of nucleotides or nucleic acids that code for a protein is called a "sense" sequence. A "recombinant DNA molecule" is understood to mean a DNA molecule which has been subjected to manipulation by molecular biology techniques.

The term "DNA coding sequence" is understood to mean a sequence of double-strand DNA which is transcribed and translated into polypeptides in a cell in vitro or in vivo when it is under the control of suitable regulatory sequences. Initiation of the coding sequence is detennined by an initiator codon at 5' aminoterminal and the end of the translation by a stop codon at 3' carboxyterminal. A polyadenylation signal (termination of the transcription) would generally be located at 3' of the coding sequence. The sequences coding the transcription and translation are regulatory RNA sequences such as promoters and stimulators and, thus, enable expression of a coding sequence in a host cell.

A "promoting" sequence is an RNA region capable of linking the RNA polymerase in the cell and initiating transcription of the coding sequence.

A "coding" sequence is under the control of transcriptional and translational sequences in the cell when the RNA polymerase transcribes the sequence coding MRNA (messenger), which is then translated into protein.

An "expression plasmid" is an extrachromosomal, circular double-strand DNA molecule that comprises regulatory sequences between which a structure gene (DNA sequence corresponding to the desired protein) is inserted. It replicates itself independently of bacteria.

An "expression vector" comprises a nucleic acid molecule and at a minimum an origin of independent replication and an inducible promoter and which can be introduced specifically into host cells such as in bacteria or eukaryote cells. Into this vector can be inserted a coding sequence called an "insert" and corresponding to the desired protein or peptide.

I—Method

1) Cell Culture

CPAE cells (calf pulmonary artery endothelial cells) were provided by Dr. J. Badet (Eukaryote Cell Biotechnology Laboratory, University of Créteil, France). These cells were cultured in an MEM medium supplemented by 20% of fetal calf serum (FCS), 2 mM of L-glutamine, 100 IU/ml of penicillin and 10 µg/ml of streptomycin (Gibco, Paisley, UK). All of the media referred to below ("complete medium") contained the same concentrations of penicillin/streptomycin and L-glutamine as that used for the CPAE cells. They are used in passages 12-20. The HMEC-1 cells (human microvasculature endothelial cells) were provided by Dr. Ades (Centers for Disease Control and Prevention, Atlanta, Ga.) who established this cell line by transfecting human dermal endothelial cells with the gene SV40 and the large antigen T. The HMEC-1 cells were cultured in complete MCDB 131 medium (Sigma, St Louis, Mo.) supplemented with 10% of FCS, 10 ng/ml of EGF (Biomedical Products Collaborative) and 1 µg/ml of hydrocortisone (Sigma). The HUVEC cells (human umbilical cord vein endothelial cells) were extracted in the umbilical cord laboratory according to the method described by Jaffe et al. The cords were subjected to controlled digestion by 0.2% collagenase A (Boehringer GmbH, Mannheim, Germany). The primary cells were cultured in complete M199 medium supplemented by 20% of FCS, 75 mM HEPES, 3.7 mM of sodium bicarbonate pH 7.5 and 5 µg/ml of fungizone (Life Technologies, France). The HMVEC-d cells (dermal microvasculature endothelial cells, Biowhittaker Europe, Belgium) were cultured from passage 4 to 6 in the complete medium supplied by the manufacturer (EGM-2MV) supplemented by 10% FCS. The C51 cells (murine colon cancer) were cultured in complete RPMI medium+ 10% FCS. The 3T3 cells (murine tumor fibroblasts) were cultured in complete DNEM medium+10%, the MDA MB 231 cells (human breast cancer cells) use the complete DMEM medium with the addition of 10% of FCS as do the cancerous fibroblast cells 3T3. The B16F10 cells (murine melanoma cells) were cultured in DMEM medium+10% FCS and 1.5 g/l of sodium bicarbonate.

The anti-disintegrin antibodies were obtained after inoculation in the rabbit of an AMEP fragment according to the method described by Herren et al. (Néosysteme, France). This fragment was constituted by 12 amino acids and contained the sequence RGDC; its molecular weight was 1.4 kDa.

2) Construction and Synthesis of Human AMEP in a Bacterial System

A fusion protein of AMEP with glutathione S-transferase (GST) was prepared. The 276-nucleotide cDNA fragment of SEQ ID NO. 1 which codes for AMEP (Met-420 to Glu-511) was amplified by polymerase chain reaction (PCR). This cDNA was subcloned in the plasmid pGEX-6P at the level of the BamH1 site (Amersham Pharmacia Biotech). Synthesis of the fusion protein GST-AMEP was induced in *Escherichia coli* DH5 α by isopropyl-1-thio-β-D-galactopyranoside (1 mM) as described by Smith and Johnson, 1988. In brief, after lysis of the bacteria with 1% Triton X100 followed by sonication, the GST-disintegrin was purified on affinity chromatography using glutathione-agarose and eluted with reduced glutathione (5 mM Tris, HCl) (ph 8.0) containing 5 mM of reduced glutathione Sigma (final pH 7.5), prepared as needed). A single band corresponding to the molecular weight of this fusion protein (36 kDa) was detected in SDS-PAGE (FIG. 1*a*).

We cleaved the AMEP of GST using a specific protease: the "PreScision™ protease" which is itself a protein coupled to a GST (Amersham, Buckinghamshire), according to the Amersham instructions to test the activity of the peptide corresponding to AMEP on the different angiogenesis models in vitro.

The AMEP was then purified by affinity chromatography using glutathione-agarose on a column according to the Sigma instructions. The AMEP was constituted of 91 amino acids and its estimated molecular mass was 9.7 kDa.

The purity of the AMEP was analyzed by Western blot (FIG. 1*b*) and high performance liquid chromatography (HPLC). The protein concentration was determined by BCA test (Pierce, Perbio, Science, France).

3) Western Blot

One hundred micrograms of purified AMEP were deposited on an electrophoresis gel constituted by 12% polyacrylamide-SDS and transferred onto a nitrocellulose membrane (Schleicher and Schuell). The membrane was saturated for 1 h with a TBS buffer (Tris buffer solution: Tris 10 mM pH 7.5; NaCl 200 mM/Tween (0.05%) containing 10% milk then incubated with a polyclonal rabbit serum at the dilution 1:1000 directed against AMEP (Neosystem, France) or with an anti-GST antibody (Amersham). After five washings in TBS/Tween, the membrane was incubated for 1 h with a suitable secondary antibody coupled with peroxidase at the dilution of 1:2000 according to the manufacture's instructions (DAKO). The membrane was washed five times in the same rinsing buffer and detection of the signal was performed according to the ECL chemoluminescence method (Amersham).

4) Adhesion of the Fibrinogen to Vitronectin and Fibronectin

First technique: punctual incubation of the endothelial cells with AMEP during the test.

The CPAE were detached from the culture plates by incubation with 1.5 mM EDTA and resuspended at the rate of $5 \times 10^5$ cells/ml in the adhesion buffer (140 mM NaCl, 10 mM Hepes, 5 mM glucose, 5.4 mM KCl, 2 mM $CaCl_2$, 1 mM $MgCl_2$, 1 mM $MnCl_2$, pH 7.4). Then, 100 µl of cell suspension was brought into the presence of AMEP (5 µg/ml) at ambient temperature then introduced into the wells of a 96-well plate (Greiner, D. Dutcher) that had been incubated in advance for one night at 4° C. with 50 µl of purified fibrinogen (40 µg/ml in PBS; Kabi), 10 µg/ml of vitronectin (Sigma); 30 µg/ml of fibronectin (Sigma) and 1% of BSA (bovine serum albumin) as negative control. After 20 minutes of incubation of the CPAE cells at 37° C., the plate was washed twice with 200 µl of adhesion buffer and the nonspecific sites were saturated with PBS supplemented with 1% of BSA for 1 hour at 37° C. The plate was then washed again twice with the adhesion buffer containing 1% of BSA. The nonadherent cells were eliminated by washing the wells three times with 200 µl of adhesion buffer plus 1% of BSA. Measurement of the phosphatase activity of the cells enabled quantification of the adherent cells. In brief, 100 µl of paranitrophenol phosphate (Sigma) at 3 mg/ml in the acetate buffer pH containing 0.1% of X100 Triton was added to the wells and incubated for 2 h at 37° C. The reaction was stopped by the addition of 1N NaOH. The release of paranitrophenol, which indicates the number of adherent cells, was measured after reading of the absorbance at 405 nm with an ELISA reader (Titertek Twin-reader). Each experiment was performed three times.

Second technique: the CPAE cells were cultured for 24 h in the presence of AMEP at the final concentration of 5 µg/ml before being detached. The remainder of the protocol was identical to the that described above with the exception that no additional incubation of the cells with AMEP was performed.

5) Model of Endothelial Cell Migration

The migration model was implemented in 24-well plates. 1.5% agarose was dissolved in the culture medium to form a gel in the wells. Half of an agarose cylinder was then inserted in a well. The CPAE cells were added to the free space left in the well and cultured until their confluence. The piece of agarose was then removed to allow the cells to migrate and AMEP was added, at the desired concentrations, to the culture medium. Then, a transparent graph paper was placed under the plate to determine the migration rate of the cells using an ocular micrometer under reverse microscope. The experiments were performed in duplicate and repeated three times. The results were expressed in percentage in relation to the control.

6) Model of Cellular Proliferation

The cells were cultured at the rate of 20,000 cells per well (96-well plate, Greiner) in the complete medium. After 24 h, the cells were cultured in a medium containing a concentration lower by half than that corresponding to the complete medium to induce the cell in phase G0/G1 of proliferation for 24 supplementary hours. The cells were then cultured for 30 h with complete medium in the presence or without the presence of AMEP. Tritiated thymidine (1 µCi per well) was then added to the cells and incubated for 18 hours. Incorporation of the tritiated thymidine by the cells was quantified by filter paper according to the protocol described for the use of a Skatron (Skatron, Lier, Norway). Radioactivity was then determined by counting after addition of scintillation liquid. The results were expressed as a percentage in relation to the control.

7) Analysis of Apoptosis and Cell Cycle (Use of Hoechst 33342) and Quantification of Early Apoptosis (Use of Annexin V).

Technique of specific vital staining of DNA with Hoechst 33342 (Sigma).

The endothelial cells (CPAE) were trypsinated and the cell suspension was adjusted to $1 \cdot 10^6$ cells/ml. Hoechst 33342 dye was added at the rate of 20 µg/ml and the cells were incubated for three minutes at ambient temperature under agitation. The percentage of apoptotic cells was analyzed by a flow cytometer (FACS). The cells were then incubated for 30 minutes in darkness (37° C.) and analysis of the cell cycle was performed.

Technique using annexin V (R and D system): A residue of $1 \cdot 10^6$ endothelial cells (CPAE) was resuspended in 1 ml of reaction buffer (100 µl of 10× binding buffer (100 mM Hepes/NaOH pH 7.4, 1.5 M NaCl, 50 mM KCl, 10 mM $MgCl_2$, 18 mM $CaCl_2$), 100 µl of propidium iodide (initial concentration 50 µg/ml), 10 µl of annexin V-FITC and 790 µl of deionized water. The suspension was incubated for 15 minutes in darkness at ambient temperature. The percentage of apoptotic cells was analyzed by flow cytometry.

8) Formation of Capillary Structures in Two Models of Fibrin Gel Angiogenesis

One of the models used the aggregates of CPAE cells according to the method described by Pepper et al., 1991. In brief, 10,000 CPAE were aggregated for 24 hours on 2% agarose on a 96-well plate. Three aggregates collected and incorporated in a fibrin gel: purified fibrinogen (3 mg/ml; Kabi) was dialyzed against MEM medium then mixed with 20% of FCS, 1% of L-glutamine, 1% of penicillin/streptomycin, 2 µM of aprotinin and AMEP at the desired concentration. Human thrombin (1 IU/ml; Sigma) was then added to obtain a fibrin gel to the surface of which was added the complete medium supplemented by aprotinin (2 µM), with this medium being changed every three days. Formation of capillary structures could be observed after 24 hours of culture. These capillaries were photographed under reverse microscope and the size of these structures was measured on the photographs. The statistical analysis (Mann-Whitney method) made it possible to determine whether the size of these structures was different.

The second model used beads on the order of 150 µm according to the technique described by Nehl et al. The cells used were HMEC-1 since CPAE could not be used in this model. The HMEC-1 cells cannot, however, be employed in the previously described model. The HMEC-1 cells adhere to the Cytodex 3 beads (Sigma) when the cells are incubated with the beads in the complete medium for 4 h at 37° C. The beads were then resuspended in a large volume of complete medium to have 30 cells/beads and agitated for 5 minutes every 30 minutes at 30 rpm for 12 h, followed by a continuous culture at the same rate for 4 days. When the entire surface of the beads was covered by cells, the beads were centrifuged at 800 g for 5 minutes to concentrate and incorporate them in a fibrin gel the same as that described for the preceding model, and the same as the methods of quantification and analysis of the results. In contrast to the model used for the CPAE, the capillary structures only appeared after 3 days of culture at 37° C.

9) Preparation of the Plasmids for Electrotransfer

The cDNA of AMEP was subcloned at the Eco RV site of the vector pBi (Clonetech, Palo Alto, Calif., USA). The expression of the gene of interest in this vector was under the dependence of a promoter responding to tetracycline in an expression system involving the eukaryote gene Tet-On. The Tet-On vector expresses the transactivator rtTA (reverse tetracycline transcriptional activator) and the vector Tet-tTS expresses the silencer tTS (tetracycline transcriptional silencer). The purifications of the plasmids were performed in a manner such that no endotoxin was present (Maxi endo free Kit, Quiagen). The purified plasmid DNA was dissolved in endotoxin-free sterile 0.9% NaCl at the desired concentration.

10) Electrotransfer of the Gene Coding for Human AMEP in the Muscle of Nude and C57B1/6 Mice 20 µg of plasmid pBi-AMEP, 10 µg of plasmid Tet-off and 20 µg of plasmid Tet-on were dissolved in 30 µl of sterile 0.9% NaCl and injected into the tibia cranial muscle of nude or C57B1/6 mice aged 8 weeks and previously anesthetized by intraperitoneal inoculation of pentobarbital as described by Mir et al. (Mir et al., 1999). In brief, 8 electric shocks of 200 V/cm were applied for 20 ms at a frequency of 1 Hz, by means of an electrode to the mouse paw and containing two steel plates. The electrode was connected to an electropulsator PS-15 (Jouan, St Herblain, France). The same plasmids not containing the AMEP gene constituted the negative control.

11) Athymic Murine Model of Tumor Growth (MDA MB 231 Cells)

The MDA-MB-231 cells, which had been previously cultured to 80% confluence, were detached, washed and resuspended in PBS at the rate of $20 \cdot 10^6$ cells/ml. Two hundred microliters of cell suspension were injected subcutaneously in the backs of 8-week-old nude mice which had been previously treated as described above. The measurements of two diameters of a tumor enabled calculation of its volume according to the mathematical formula (sum of the two diameters divided by $2)^3/0.52$. When the tumors reached a volume of 18 $mm^3$, doxycycline (stable analog of tetracycline) (Sigma-Aldrich, Saint Quentin Fallavier, France) at 200 µg/ml was added to the mice's drinking water and supplemented with 5% of sucrose to induce expression of AMEP in the muscles of the mice. The size of the tumors was monitored for 14 days after induction.

12) Quantification of the Tumoral Angiogenesis (Immunohistochemistry and Image Analysis of the Subcutaneous Solid Tumors)

The tumor tissues were fixed in ethanol. Sections of 5 μm were prepared in paraffin. The endogenous peroxidase was extinguished by 3% of $H_2O_2$ for 10 minutes so that the sections could be used in immunohistochemistry. After washing the sections with distilled water then saturation with 1:10 Optimax serum (BioGenex, San Ramon, Calif.) for 10 minutes, the slides were incubated for 1 h with an anti-CD31 rat antibody (endothelial cell adhesion molecule) at 1:50. After two washings with Optimax for 4 minutes, the slides were incubated with an anti-rat goat polyclonal antibody coupled to biotin (1/50) followed by two 4-minute washings with Optimax. The slides were then treated with a DAB chromogenic substrate for 10 minutes, washed with distilled water, counterstained with Mayer's hematoxylin and mounted on Pertex. All of the slides were immunotagged and counterstained on the same day to ensure a standardized intensity of the tagging.

For each animal, a representative histological sample of the sections tagged with CD31 was subjected to image analysis using an AxiophotZeiss microscope (Germany) and a Sony 3CCD camera (resolution 768×576 pixels). Selection of an enlargement×100 allowed digitization of the totality of the sample. Only the tumor tissue was taken into account, with the necrotic and fibrinous zones being excluded. For each sample, the totality of the surface—or 8 contiguous fields if the size of the sample was too large—was digitized. The images were analyzed with a specific Linux-based program producing a quantitative index from 0 to 255. The digitized color images were transformed into different levels of gray. A theoretical image composed solely of brown-red vessels would correspond to an index of 255, whereas an image lacking in vessels (stained blue in its entirety) would be associated with an index of 0. A value comprised between 0 and 255 was associated with each pixel of the image and the mean of these values was obtained for each image. The final index for each animal was the result of the calculation of the mean value of 8 contiguous fields.

13) Syngenic Metastatic Tumor Model (Pulmonary Metastases, B16F10 Cells)

Doxycycline (Sigma-Aldrich) at 200 μg/ml was added to the drinking water of C57B1/6 mice to induce expression of AMEP in the muscles of the mice three day before injection of B16F10 mouse melanoma cells. These cells were first cultured up to 50% confluence, detached, washed and resuspended in PBS at the rate of $4 \neq 10^6$ cells/ml. One hundred microliters of cell:suspension were injected intravenously in the retro-orbital sinus of the mice. The mice were sacrificed 7 days after the transplant of the cells, the cells were collected and a counting of the pulmonary metastases of black color was performed under a binocular loupe.

II—Results

1) Inhibition of the Adhesion of Endothelial Cells by AMEP on Fibronectin, Vitronectin and Fibrinogen The two adhesion techniques described in the Methods section were performed in the presence of AMEP or of a 1.4-kDa fragment of AMEP constituted of 12 amino acids with the sequence RGDC (residues 65-68 of SEQ ID NO: 2) (Néosystem, France). This peptide ("1.4-kDa peptide") was used to determine whether the mode of action of AMEP differs from that of a control RGD peptide.

When the endothelial cells were incubated punctually for 30 minutes with the 1.4-kDa peptide (1 μg/ml) prior to the adhesion test, a strong reduction in the adhesion of the cells was observed on vitronectin (49±1.2% of inhibition) and on fibrinogen (50±2.4% of inhibition). This result is not surprising in that this fragment blocks the interaction of the alpha v beta 3 integrins present at the surface of the endothelial cells at their privileged substrates. Under these same conditions, no significant effect of AMEP on adhesion of the endothelial cells at these substrates was detected at a comparable molar concentration (10 μg/ml, not shown).

Figure 2:
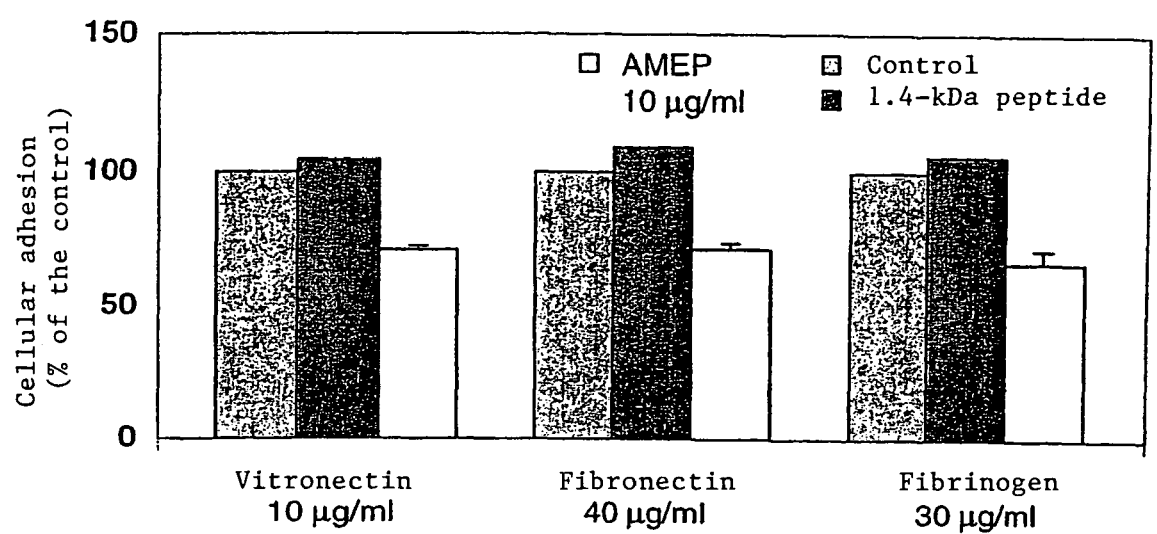
FIG. 2 shows the effect of AMEP on the adhesion of CPAE to fibrinogen (30 μg/ml), vitronectin (10 μg/ml) and fibronectin (40 μg/ml). The cells were pretreated for 24 h with AMEP or the 14-amino-acid fragment prior to the adhesion test (description in Materials and methods). The experiments were performed in triplicate and repeated three times. The results are expressed in percentage in relation to the control (mean±SEM).

In contrast, when the cells were preincubated for 24 h with AMEP or with the 1.4-kDa peptide at the same molar concentration as described above, the results obtained were reversed: AMEP inhibited adhesion of the endothelial cells on vitronectin, fibronectin and fibrinogen by 30% for the three substrates, whereas the 1.4-kDa peptide had no significant effect (FIG. 2).

2) Inhibition of the Migration of Endothelial Cells by AMEP

Figure 3:
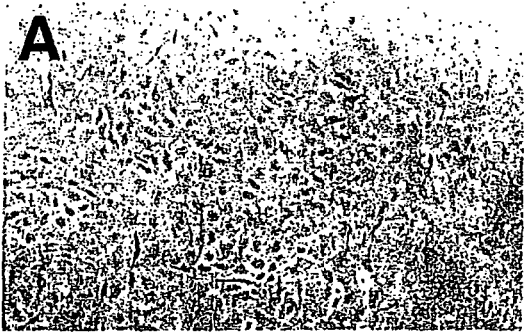
FIG. 3 shows the effect of AMEP on the morphology and migration of endothelial cells. The migration front is represented on the photographs B, D, E, respectively, control conditions, AMEP at 5 μg/ml and 10 μg/ml (phase-contrast microscopy).
Figure 3:
Figure 3:
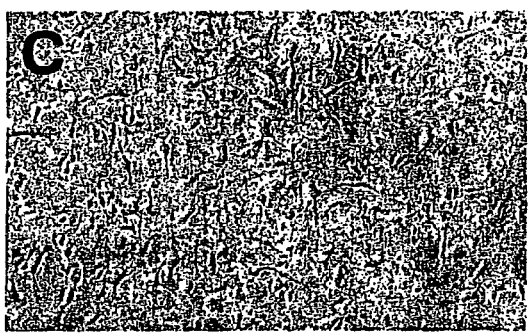
Figure 3:
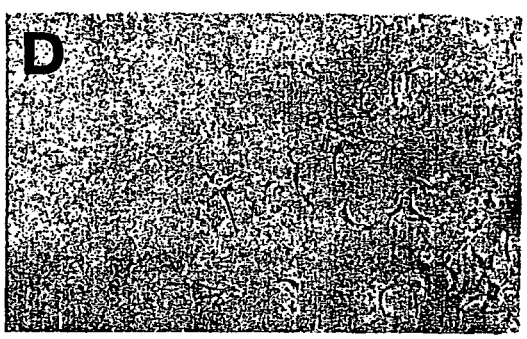
Figure 3:
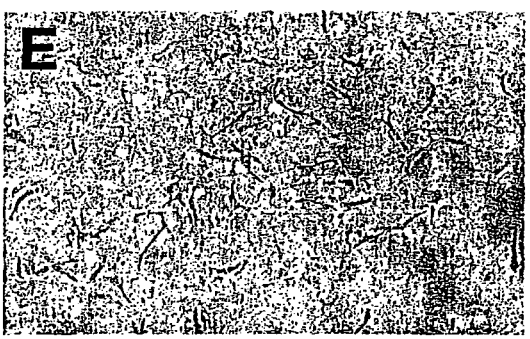
Figure 3:
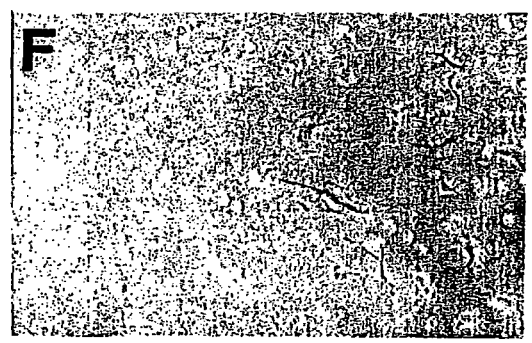
Figure 4:
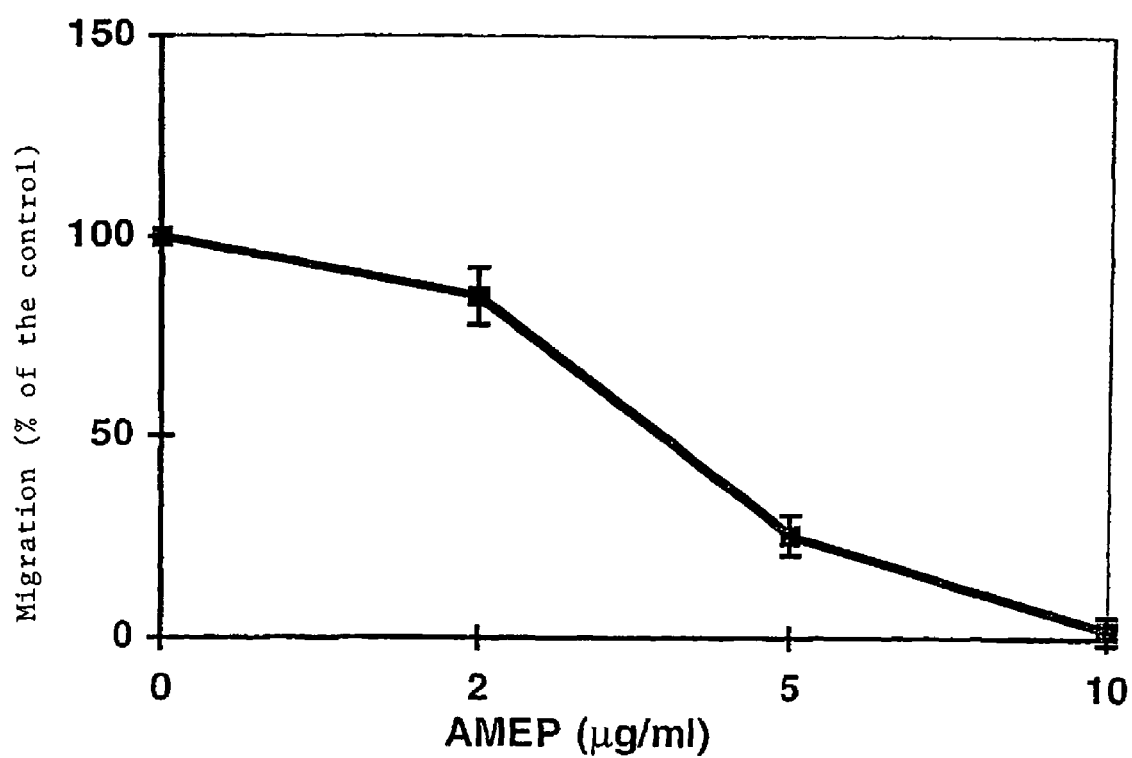
FIG. 4 represents the dose-dependent inhibition of the migration of CPAE by AMEP. The position of the migration front of the cells was measured every day over a 3-day period. The results are the mean of five experiments and are expressed as percentage in relation to the control: mean±SEM.

FIG. 3 shows the appearance of endothelial cells (CPAE) after addition of AMEP at 5 μg/ml (C, D) and 10 μg/ml (E, F) compared to the control (absence of the domain: A, B) in our migration model. A very clear morphological change in the cells is observed in the presence of AMEP: the endothelial cells form long pseudopodia and cohesion of the cells with each other deteriorates with numerous cells becoming detached (10 μg/ml). This phenomenon is even more visible at the migration front of the cells (D, F). The effect of AMEP on the displacement rate of these cells is dose dependent (2-10 μg/ml) with a complete inhibition of cell migration at 10 μg/ml (FIG. 4) in contrast to the 1.4-kDa peptide (1 μg/ml) which does not induce any inhibitory effect.

3) Effect of AMEP on Cell Proliferation

Figure 5:
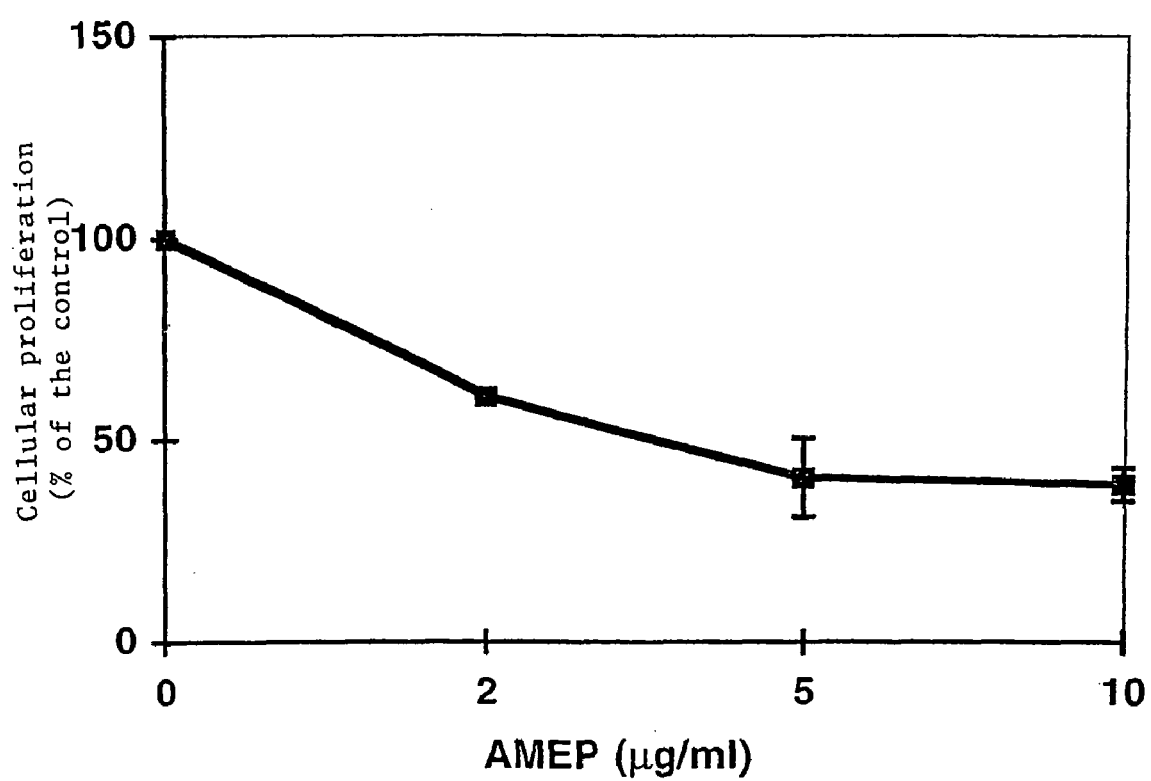
FIG. 5 represents the dose-dependent inhibition of the proliferation of CPAE by AMEP. The cells were cultured for 48 h in the presence of AMEP or a fragment of this domain containing the sequence RGDC (residues 65-68 of SEQ ID NO: 2) and incubated with 1 μCi of tritiated thymidine for 18 h. The incorporated radioactivity was then measured. The results are the mean of five experiments and are expressed in percentage in relation to the control: mean±SEM.

In contrast to the 12-amino-acid fragment (1.4-kDa peptide), which has no effect on the proliferation of endothelial cells no matter what concentration is employed (1-100 μg/ml, not shown), AMEP strongly inhibits their proliferation (reduction of 40%) beginning at 2 μg/ml (FIG. 5). This effect is maximal at 5 μg/ml with 60% inhibition of proliferation (identical percentage at 10 μg/ml). It should be noted that the polyclonal rabbit serum, previously used in Western blot (Néosystem, France), directed against AMEP, inhibits in a comparable manner proliferation of these cells (65±0.1%).

To analyze the specificity of action of AMEP, we studied its effect on the proliferation of primary endothelial cells from the macrovasculature or microvasculature as well as cancer cells known to possess or not to possess the integrin alpha v beta 3 at their surface, one of the known targets of AMEP. The results presented in Table 1 below show that AMEP inhibits in a comparable manner different types of endothelial cells, whereas it has no effect on proliferation of cancer cells of diverse origin (fibroblastic, breast, colon) which have little or no integrin alpha v beta 3 at their surface (MDA MB 231, C51, 3T3, respectively). A noteworthy effect of AMEP is advantageously observed on the proliferation of cells expressing the integrin alpha v beta 3.

TABLE 1

| | Cell type | | | | | | |
|---|---|---|---|---|---|---|---|
| | Endothelial cells | | | Cancer cells | | | |
| | Bovine CPAE | Human HMVEC-d | Human HMVEC | Murine 3T3 | Murine C51 | Human MDA-MB-231 | B16F10 |
| % inhibition of cell proliferation by AMEP (5 μg/ml) | 60.4 ± 3.2 | 54.2 ± 2.1 | 52.6 ± 3.1 | 9.1 ± 2.2 | 0.5 ± 1.1 | 17.5 ± 0.5 | 74.3 ± 7.0 |

Table 1 shows the effect of AMEP on the proliferation of endothelial and cancer cells. The experiments were repeated five time (mean±SEM). The values shown represent the percentage of inhibition of proliferation of the indicated cells by AMEP used at the rate of 5 μg/ml compared to the control (absence of AMEP) performed under the same conditions.

4) Demonstration of the Proapoptotic Activity of AMEP on Endothelial Cells

Two techniques were employed to determine the percentage of apoptotic cells. One technique used Hoechst 33342 to keep the cells alive and monitor the phases of the cell cycle. The technique using annexin-V enabled determination of early apoptosis of the endothelial cells (visualization of the serine phosphatidyls at their surface). The results obtained are comparable, i.e., a percentage of apoptotic cells multiplied by 3 in the presence of AMEP (Table 2 below). In contrast, contrary to most molecules that induce apoptosis, no modification of the cell cycle was found with Hoechst 33342 in the presence of AMEP (not shown).

TABLE 2

| | | Hoechst 33342 method | Annexin-V method |
|---|---|---|---|
| % of apoptotic cells | Control | 3.9 ± 1.1 | 4.6 ± 0.9 |
| | AMEP 5 μg/ml | 12.6 ± 3.7 | 12.8 ± 2.5 |

Table 2 shows the percentage of cells in apoptosis. The flow cytometry analyses were performed according to the two methods described in the Materials and methods section. The experiments were performed three times. Mean±SEM.

Figure 6:
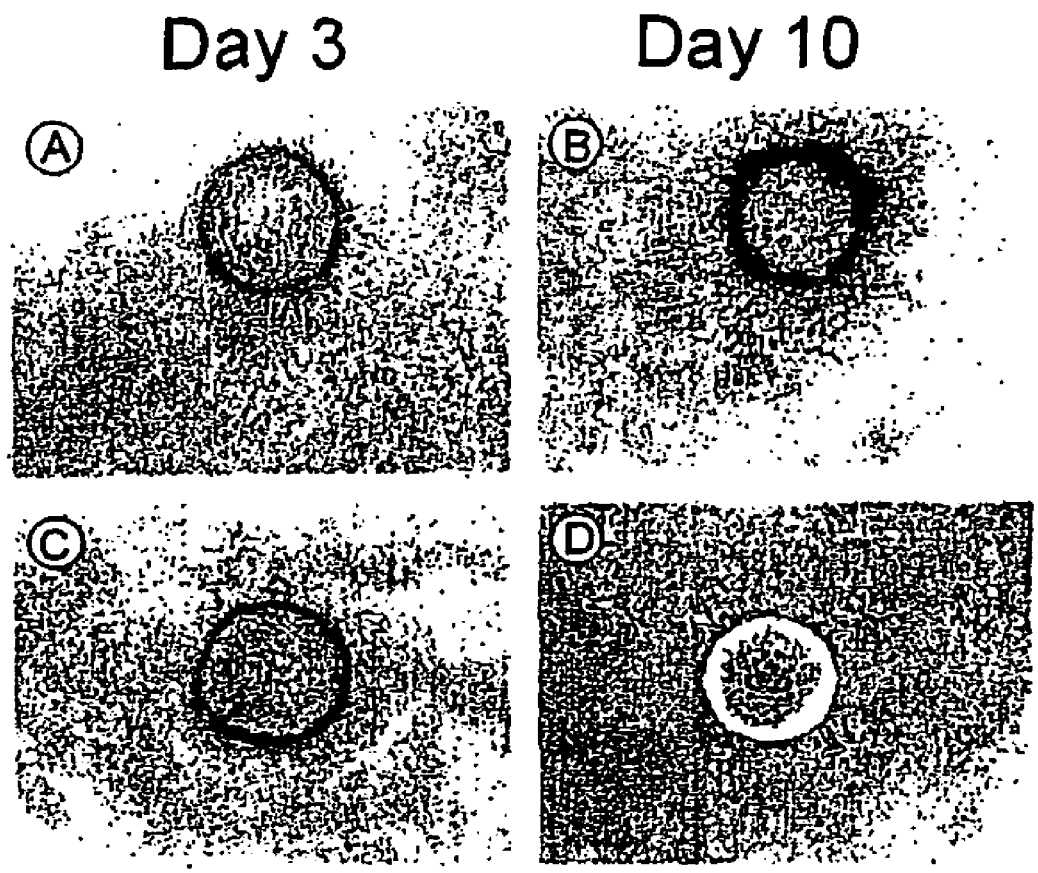
FIG. 6 shows the effect of AMEP on the formation of capillary structures using HMEC-1. Cytodex beads covered with endothelial cells were incorporated in a fibrin gel in the absence of AMEP (photographs A, B) and in the presence of AMEP (5 μg/ml) (photographs C, D).
Figure 7:
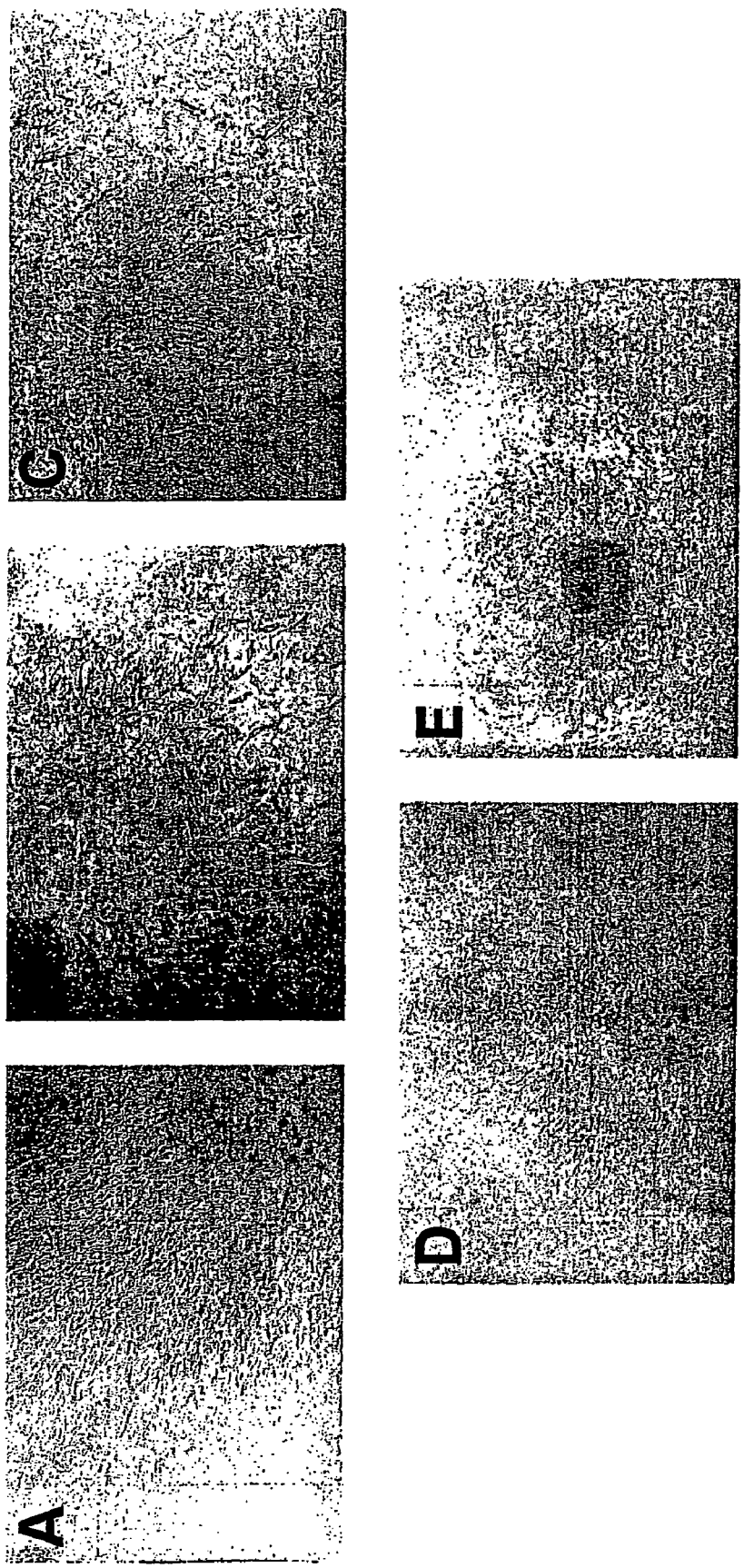
FIG. 7 shows the effect of AMEP on the formation of capillaries in fibrin gel using CPAE in the presence of 5 μg/ml (B) and 10 μg/ml (C, E) of AMEP in relation to the control (A, D).

5) AMEP Inhibits the Formation of Capillary Structures in two Fibrin Gel Angiogenesis Models Endothelial cells of the microvasculature are more suitable for studying angiogenesis which is why we used HMEC-1 cells (Nehls and Herrmann, 1995). These cells were cultured on beads and then incorporated in a fibrin gel (FIG. 6, control: A, B). The inhibitory effect of AMEP (5 μg/ml) on formation of capillary structures was observed after three days of culture (C) and became spectacular after 10 days with a 90% reduction in the size of the tubes (D). Since the prior studies were intended to determine the effects of AMEP on different stages of angiogenesis employing CPAE as endothelial cells, we wanted to verify the effect of this domain on another model of angiogenesis. These cells can only be used in the model using beads because their morphology is not adapted. Aggregation of CPAE was the sole means of studying the effect of AMEP on angiogenesis in vitro. The capillary structures appeared 24 h after incorporation of the aggregates in the fibrin gel. FIG. 7 brings together photographs taken after 3 days of incubation. The addition of AMEP at 5 μg/ml (B) or 10 μg/ml (C, E) induced a disorganization of capillary structures compared to the control (A, D) leading to the death of the endothelial cells (not shown). Under the control conditions, an increase in the length of the structures was observed up to 6 days of incubation (not shown).

6) Inhibition of Tumor Growth and Tumor Angiogenesis by AMEP on Nude Mice.

Production of AMEP in nude mice was obtained after electrotransfer of the gene coding for AMEP in the mouse muscle, followed by induction of its expression by doxycycline.

Figure 8:
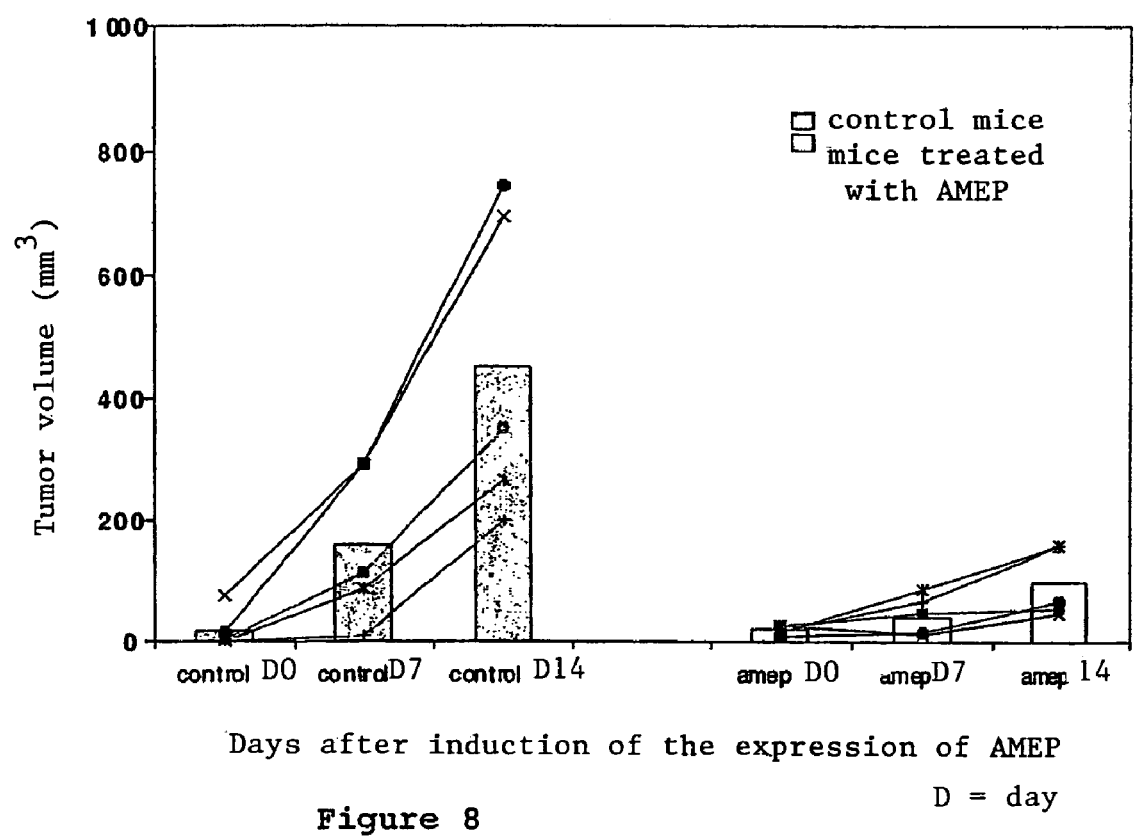
FIG. 8 shows the inhibition of tumor growth by AMEP. Each point of the curve represents the volume of the tumor measured on a nude mouse. The experiment comprised five animals for the control group as well as five animals for the AMEP group, treated for 14 days. The histograms represent the mean tumor volume of 5 mice for each group. This figure is representative of 3 distinct experiments.

As shown in FIG. 8, the tumor volume of the AMEP group is markedly smaller than that of the control group with a confirmed inhibition that reached 78% after 14 days of treatment. A similar percentage of inhibition was observed after only 7 days of treatment. Quantification of the intratumoral angiogenesis was implemented on the sections of these tumors. The results presented in Table 3 (below) show that the powerful inhibitory effect of AMEP on tumor growth is correlated with a significant inhibition of the number of vessels within the tumors treated with AMEP of 53.4%.

The results show that AMEP acts powerfully on the in vivo tumor models not expressing the integrin alpha v beta 3.

Table 3 below shows the statistical index of tumor vascularization obtained after digitization and computerized image analysis of a representative sample of tumor sections originating from mice expressing or not expressing AMEP.

TABLE 3

| | Control group | Group treated with AMEP |
|---|---|---|
| Mean | 2.96 | 1.38 |
| Variance | 0.28 | 0.14 |

7) Inhibition of the Formation of Pulmonary Metastases by AMEP on Syngenic Mice

Figure 9:
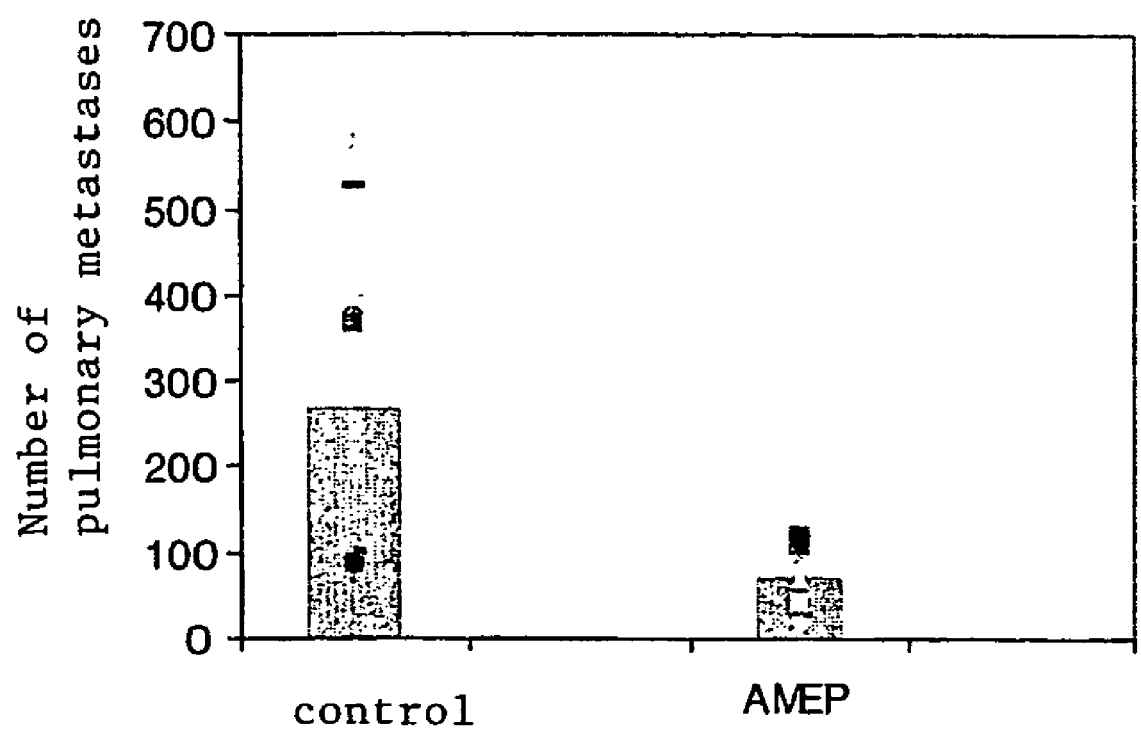
FIG. 9 shows the inhibition of the number of pulmonary metastases by AMEP using melanoma cells. Each point represents the number of metastases counted in the lung of a C57B1/6 mouse. The experiment presented comprised 12 animals for each group. The histogram shows the mean of the number of metastases in the control and treated group. This experiment is representative of two distinct experiments.
Figure 10:
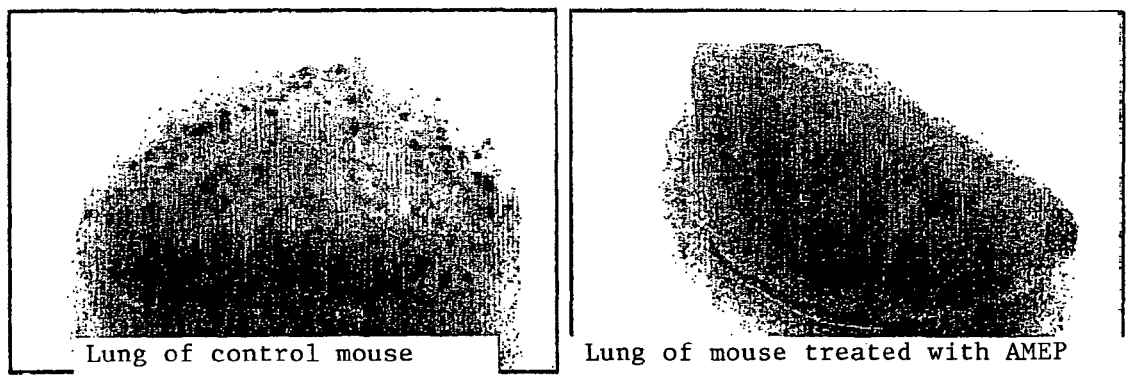
FIG. 10 shows a photographic representation of the inhibition of the number of pulmonary metastases (black spots) of a C57B1/6 mouse lung treated with AMEP in comparison with a control mouse lung.

Production of AMEP in the muscle of C57B1/6 mice was induced by doxycycline. An exceptional inhibition of the number of pulmonary metastases of 74.2% after 7 days of treatment was observed in the group of mice treated by AMEP compared to the control group (FIGS. 9 and 10).

Endothelial cells are activated and acquire an angiogenic phenotype during the angiogenic process. They then possess at their surface the integrin alpha v beta 3 and metargidin (molecules undetectable on endothelial cells stemming from mature vessels) (Herren et al., 1997).

The set of results obtained show that AMEP possesses an antiangiogenic activity that is greater than that of the 1.4-kDa peptide. Given that both AMEP and the 1.4-kDa peptide possess an RGD sequence implicated in bonding endothelial cells to alpha v beta 3 integrins, we believe that the action of AMEP is not limited to blocking the functions of the alpha v beta 3 integrin. AMEP appears to possess its own activity which could be linked to modifications of the signalization at the cellular level (message that could be transported by the integrin alpha v beta 3 and/or metargidin).

Cell adhesion is a phenomenon which intervenes in cell migration. However, we believe that inhibition of adhesion is not the sole mechanism responsible for inhibition of migration of endothelial cells. Thus, 10 µg/ml of AMEP is sufficient to totally block migration of endothelial cells, whereas, at this same concentration, the inhibitory effect of AMEP on adhesion is only partial.

This exceptional inhibitory activity of AMEP on the key stages of angiogenesis is reinforced by its antiproliferative effect (up to 60% inhibition of endothelial cells). It is noteworthy that inhibition of proliferation of endothelial cells induced by AMEP is not associated with a detectable modification of the cell cycle.

During the final stage of angiogenesis, the cells are organized into tubes which anastomose together to enable formation of a vascular lumen. We have recreated this phenomenon in vitro with microvasculature endothelial cells (HMEC-1) and macrovasculature endothelial cells (CPAE) by means of the two techniques described in the Materials section. In a remarkable manner, total inhibition of the formation of capillary structures was observed in the model using HMEC-1 in the presence of AMEP. In contrast to that which we had observed until now with other inhibitors of angiogenesis, AMEP induces a lethal disorganization of the CPAE tubes previously formed on an early basis (12 h). The CPAE have a proliferation and migration rate higher than that of the HMEC-1 (not shown), which can explain the duality of the effect of AMEP on the two angiogenesis models.

These research studies also show that inhibition of tumoral angiogenesis in vivo by AMEP leads to an exceptional inhibition of tumor growth, even for tumors known to not express the integrin alpha v beta 3. Moreover, a pronounced antimetastatic effect of AMEP in a pulmonary metastasis model was demonstrated.

Finally, the treatment of endothelial cells with 10 µg/ml of AMEP induced an augmentation of the number of dead endothelial cells (floating in the culture medium) that could be seen with the phase-contrast microscope (FIG. 3). Nevertheless, the effect of this product on apoptosis (phenomenon quantifiable on still living cells) was modest (augmentation by a factor of 3). AMEP, thus, has the particular characteristic of associating a powerful antiangiogenic effect with an induction of cell death by a phenomenon recently described under the name of anoikis (Frisch, 2000; Zhu et al., 2001).

The innovative aspect of AMEP, thus, is based on its capacity to inhibit the stages of angiogenesis including the migration and proliferation of endothelial cells, which differentiates it from other molecules discovered to date (cf. angiostatin which inhibits the proliferation of endothelial cells, O'Reilly et al., 1994; Wu et al., 1997; Sim et al., 1997) or endostatin which also inhibits their proliferation as well their migration, but solely when this migration is induced by an angiogenic factor such as VEGF or bFGF (O'Reilly et al., 1998, Sim et al., 2000; Yamaguchi et al., 1999). Moreover, the respective effects of AMEP on migration and angiogenesis in vitro are spectacular: substantially complete shutdown of the mobility of the endothelial cells and absence of formation of capillary structures.

Unexpectedly, the powerful inhibitory effects of AMEP, synthesized in the form of recombinant protein in bacteria, on the total set of in vitro experiments described were confirmed by the results obtained in vivo performed with AMEP synthesized de novo in mammals. The inhibitory effect of AMEP on tumor growth in the athymic model is advantageously seen in relation to a diminution of the number of intratumoral vessels, a direct consequence of the inhibition by AMEP, in all stages of angiogenesis in vitro. Moreover, the anti-invasive effect of AMEP on formation of pulmonary metastases using melanoma cells correlated with the particular antiproliferative effect of AMEP on these same cells in vitro.

BIBLIOGRAPHIC REFERENCES

Brooks, P. C., Clark, R. a. & Cheresh, D. A., (1994). Requirement of vascular integrin alpha v beta 3 for angiogenesis. Science 264, 569-571.

Eliceiri, B. P., Klemke, R., Stromblad, S. & coll., (1998). Integrin alpha v beta3 requirement for sustained mitogen-activated protein kinase activity during angiogenesis. 140, 1255-1263.

Eliceiri, P. B. & Cheiresh, A., (2000). Role of alpha v. integrins during angiogenesis. Cancer J. 6 (suppl: 3), S245-S249.

Folkman, J., (1984). What is the role of endothelial cells in angiogenesis? Lab. Invest. 51, 601-604.

Hammes, H. P., Brownlee, M., Jonczyk, A., & coll., (1996). Subcutaneous injection of a cyclic peptide antagonist of vitronectin receptor-type integrins inhibits retinal neovascularization. Nat. Med. 2, 529-533.

Frisch, S. M., (2000). Anoikis. Methods Enzymol., 322, 472-479.

Herren, B., Raines, E. & Ross, R., (1997). Expression of a disintegrin-like protein in cultured human vascular cells and in vivo. FASEB J., 11, 173-180.

Howard, L., Nelson, K. K., Maciewicz, R. A. & Blobel, C., (1999). Interaction of the metalloprotease disintegrins MDC9 and MDC15 with two SH3 domain-containing proteins, endophilin I and SH3PX1. J. Biol. Chem., 274, 31693-31699.

Jaffer, E. A., Hoyer, L. W. & Nachman, R. L., (1973). Synthesis of antihemophilic factor antigen by cultured human endothelial cells. J. Clin. Invest., 52, 2757-2764.

Kang, I-C., Lee, Y-D & Kim, D-S., (1999). A novel disintegrin salmosin inhibits tumor angiogenesis. Cancer research, 59, 3754-3760.

Kostetsky, P. V. & Artemjev., I. V., (2000). Conformational analysis of the biologically active RGD-containing anti-adhesive peptide cyclo (ArgGlyAspPhe-D-val). Biochemistry, 65, 1041-1048.

Klein, S., Glancotti, F., Presta, M., Albelda, S., Buck, C. A. & Rifkin, D. B., (1993). Basic fibroblast growth factor modulates integrin expression in microvascular endothelial cells. Mol. Biol. Cell., 4, 973-982.

Krätschmar, J., Lum, L. & Blobel, C., (1996). Metargidin, a membrane-anchored metalloprotease-disintegrin protein with an RGD integrin binding sequence. J. Biol. Chem., 271, 4593-4596.

Mir, L. M., Bureau, M F., Gehl, J., Rangara, R., Rouy, D., Caillaud, J M., Delaere, P., Branellec, D., Schwartz, B. and Scherman, D., (1999). High-efficiency gene transfer into skeletal muscle mediated by the electric pulses. Pro. Natl. Acad. Sci. USA, 96, 4262-4267.

Nehls, V. & Herrmnann, R., (1995). The configuration of fibrin clots determines capillary morphogenesis and endothelial cell migration. Micsrovasc. Res., 50, 311-322.

O'Reilly, M. S., Holmgren, L., Shing, Y., Chen, C., Rosentahl, R. A., Moses, M., Lane, W. S., Cao, Y., Sage, E. H. & Foldman, J., (1994). Angiostatin, a novel angiogenesis inhibitor that mediates the suppression of metastasis by Lewis lung carcinoma. Cell 79, 315-328.

O'Reilly, M. S., Boehm, T., Shing, Y., Fukai, N., Vasios, G., Lane, W. S., Flynn, E., Birkhead, J. R., Olsen, B. R. &

Foldman, J., (1997). Endostatin: endogeneous inhibitor of angiogenesis and tumor growth. Cell 88, 277-285.

Pepper, M. S., Montesano, R., Vassali, J. D. & Orli, L., (1991). Chondrocytes inhibit endothelial sprout formation in vitro: evidence for involvement of a transforming growth factor-beta., J. Cell. Physiol., 146, 170-179.

Primakoff, P. & Myles, D. G., (2000). The ADAM gene family surface proteins with adhesion and protease activity. TIG 16, 83-87.

Sim, B. K., O'Reilly, M. S., Liang, H., Fortier, A. H., He, W., Madsen, J. W., Lapcevich, R. & Nacy, C. A., (1997). A recombinant human angiostatin protein inhibits experimental primary and metastatic cancer. Cancer Res. 57, 1329-1334.

Smith, D. B. & Johnson, K. S., (1988). Single-step purification of polypeptides expressed in Escherichia coli as fusions with glutathion S-transferase. Gene 67, 31-40.

Sim, B. K., MacDonald, N. J. & Gubish, E. R., (2000). Angiostatin and endostatin: endogenous inhibitors of tumor growth. Cancer Metastasis Rev., 19, 181-190.

Wolfsberg, T., Primakoff, P., Myles, D. G. & White, J. M. ADAM, (1995). A novel family of membrane proteins containing a disintegrin and metalloprotease domain: multipotential functions in cell-cell and cell-matrix interactions. J. Cell. Biol., 131, 275-278.

Wu, Z., O'Reilly, M. S., Foldman, J. & Shing, Y., (1997). Suppression of tumor growth with recombinant murine angiostatin. Biochem. Biophys. Res. Commun., 236, 651-654.

Yamaguchi, N., Anand-Apte, B., Lee, M., Sasaki, T., Fukai, N., Shapiro, R., Que, I., Lowik, C., Timpl, R. & Olsen, B. R., (1999). Endostatin inhibits VEGF-induced endothelial cell migration and tumor growth independently of zinc binding. EMBO J., 18, 4414-4423.

Yeh, C H., Peng, H-C., Huang, T-F., (1998). Accutin, a new disintegrin, inhibits angiogenesis in vitro and in vivo by acting as integrin alpha v beta 3 antagonist and inducing apoptosis. Blood, 92, 3268-3276.

Zhang, X-P., Kamata, T., Yokoyama, K., McLaughlin, W., Takada, Y., (1998). Specific interaction of the recombinant disintegrin-like domain of MDC-15 (metargidin, ADAM-15) with integrin alpha v beta 3. J. Biol. Chem., 273, 7345-7350.

Zhu, Z., Sanchez-Sweatman, O., Huang, X., Wiltrout, R., Khokha, R., Zhao, Q., Gorelik, E., (2001). Anoikis and metastatic potential of cloudman S91 melanoma cells. Cancer Res., 61, 1707-1716.

The invention claimed is:

1. A method of treating a mammal with melanoma by decreasing the number of intratumoral vessels associated with the melanoma, or inhibiting the formation of new intratumoral vessels therein, the method comprising administering by:
 a) injection in the tumor of the mammal of a therapeutically effective amount of an expression plasmid comprising a polynucleotide coding for a therapeutic peptide consisting of SEQ ID NO:2 absent any operably linked coding sequence, wherein the polynucleotide sequence is operably linked to a promoter or an expression control sequence, followed by application of electrical pulses to the site of injection in the tumor of the mammal; or
 b) injection in a muscle of the mammal of a therapeutically effective amount of an expression plasmid comprising a polynucleotide coding for a therapeutic peptide consisting of SEQ ID NO:2 absent any operably linked coding sequence, wherein the polynucleotide sequence is operably linked to a promoter or an expression control sequence, followed by application of electrical pulses to the site of injection in the muscle of the mammal;
 whereby the expression of SEQ ID NO:2 decreases the number of intratumoral vessels associated with the melanoma or the formation of new intratumoral vessels therein and the melanoma in the mammal is treated.

2. The method according to claim 1, wherein said polynucleotide sequence consists of SEQ ID NO: 1.

3. The method according to claim 1, wherein said expression plasmid coding for the therapeutic peptide consisting of SEQ ID NO: 2 is administered by injection in said muscle of the mammal with melanoma followed by application of electric pulses to the site of the injection in said muscle of the mammal with melanoma.

4. A method of treating a mammal with pulmonary metastases by decreasing the number of intratumoral vessels associated with the pulmonary metastases, or inhibiting the formation of new intratumoral vessels therein, the method comprising administering by:
 injection in a muscle of the mammal of a therapeutically effective amount of an expression plasmid comprising a polynucleotide coding for a therapeutic peptide consisting of SEQ ID NO:2 absent any operably linked coding sequence, wherein the polynucleotide sequence is operably linked to a promoter or an expression control sequence, followed by application of electrical pulses to the site of injection in the muscle of the mammal;
 whereby the expression of SEQ ID NO:2 decreases the number of intratumoral vessels vessels associated with the pulmonary metastases or the formation of new intratumoral vessels therein and the pulmonary metastases in the mammal are treated.

5. The method according to claim 4, wherein said polynucleotide sequence consists of SEQ ID NO: 1.

* * * * *

```
SEQUENCE LISTING

<160> NUMBER OF SEQ ID NOS: 2

<210> SEQ ID NO 1
<211> LENGTH: 276
<212> TYPE: DNA
<213> ORGANISM: Homo sapiens
<220> FEATURE:
<221> NAME/KEY: CDS
<222> LOCATION: (1)..(276)
<223> OTHER INFORMATION: Coding sequence for the disintegrin domain of
      the metargidin

<400> SEQUENCE: 1 atg gct gct ttc tgc gga aat atg ttt gtg gag ccg ggc gag cag tgt      48
Met Ala Ala Phe Cys Gly Asn Met Phe Val Glu Pro Gly Glu Gln Cys
 1               5                  10                  15 gac tgt ggc ttc ctg gat gac tgc gtc gat ccc tgc tgt gat tct ttg      96
Asp Cys Gly Phe Leu Asp Asp Cys Val Asp Pro Cys Cys Asp Ser Leu
             20                  25                  30 acc tgc cag ctg agg cca ggt gca cag tgt gca tct gac gga ccc tgt     144
Thr Cys Gln Leu Arg Pro Gly Ala Gln Cys Ala Ser Asp Gly Pro Cys
         35                  40                  45 tgt caa aat tgc cag ctg cgc ccg tct ggc tgg cag tgt cgt cct acc     192
Cys Gln Asn Cys Gln Leu Arg Pro Ser Gly Trp Gln Cys Arg Pro Thr
     50                  55                  60 aga ggg gat tgt gac ttg cct gaa ttc tgc cca gga gac agc tcc cag     240
Arg Gly Asp Cys Asp Leu Pro Glu Phe Cys Pro Gly Asp Ser Ser Gln
 65                  70                  75                  80 tgt ccc cct gat gtc agc cta ggg gat ggc gag taa                     276
Cys Pro Pro Asp Val Ser Leu Gly Asp Gly Glu
                 85                  90

<210> SEQ ID NO 2
<211> LENGTH: 91
<212> TYPE: PRT
<213> ORGANISM: Homo sapiens

<400> SEQUENCE: 2
```

-continued

```
Met Ala Ala Phe Cys Gly Asn Met Phe Val Glu Pro Gly Glu Gln Cys
 1               5                  10                  15

Asp Cys Gly Phe Leu Asp Asp Cys Val Asp Pro Cys Cys Asp Ser Leu
                20              25                  30

Thr Cys Gln Leu Arg Pro Gly Ala Gln Cys Ala Ser Asp Gly Pro Cys
        35                  40              45

Cys Gln Asn Cys Gln Leu Arg Pro Ser Gly Trp Gln Cys Arg Pro Thr
        50              55                  60

Arg Gly Asp Cys Asp Leu Pro Glu Phe Cys Pro Gly Asp Ser Ser Gln
 65              70                  75                  80

Cys Pro Pro Asp Val Ser Leu Gly Asp Gly Glu
                85              90
```